(12) United States Patent
Lubenau et al.

(10) Patent No.: US 10,815,455 B2
(45) Date of Patent: *Oct. 27, 2020

(54) SALMONELLA-BASED VECTORS FOR CANCER IMMUNOTHERAPY TARGETING WILMS' TUMOR GENE WT1

(71) Applicant: VAXIMM AG, Basel (CH)

(72) Inventors: Heinz Lubenau, Neustadt an der Weinstrasse (DE); Marco Springer, Wendlingen (DE)

(73) Assignee: Vaximm AG (CH)

(*) Notice: Subject to any disclaimer, the term of this patent is extended or adjusted under 35 U.S.C. 154(b) by 23 days.

This patent is subject to a terminal disclaimer.

(21) Appl. No.: 15/872,750

(22) Filed: Jan. 16, 2018

(65) Prior Publication Data
US 2018/0163169 A1 Jun. 14, 2018

Related U.S. Application Data

(63) Continuation of application No. 14/786,652, filed as application No. PCT/EP2014/001099 on Apr. 24, 2014, now Pat. No. 9,920,297.

(30) Foreign Application Priority Data

Apr. 25, 2013 (EP) .................................. 13002245

(51) Int. Cl.
| | |
|---|---|
| *C12N 1/20* | (2006.01) |
| *A61K 35/74* | (2015.01) |
| *C07K 14/47* | (2006.01) |
| *C12R 1/42* | (2006.01) |
| *A61K 35/00* | (2006.01) |
| *A61K 39/00* | (2006.01) |

(52) U.S. Cl.
CPC ............... *C12N 1/20* (2013.01); *A61K 35/74* (2013.01); *C07K 14/4748* (2013.01); *C12R 1/42* (2013.01); *A61K 39/00* (2013.01); *A61K 2035/11* (2013.01); *A61K 2039/523* (2013.01); *Y02A 50/484* (2018.01)

(58) Field of Classification Search
None
See application file for complete search history.

(56) References Cited

U.S. PATENT DOCUMENTS

| 5,726,288 | A | 3/1998 | Call et al. | |
| 9,920,297 | B2* | 3/2018 | Lubenau | A61K 35/74 |
| 10,221,224 | B2* | 3/2019 | Scheinberg | A61K 39/0011 |
| 2006/0068469 | A1* | 3/2006 | Payne | A61K 48/0008 435/69.1 |
| 2007/0092968 | A1* | 4/2007 | Ji | A61K 48/0058 435/456 |
| 2007/0207170 | A1 | 9/2007 | Dubensky et al. | |
| 2012/0076752 | A1 | 3/2012 | Wu et al. | |
| 2016/0068801 | A1 | 3/2016 | Lubenau et al. | |
| 2016/0317634 | A1 | 11/2016 | Springer et al. | |

FOREIGN PATENT DOCUMENTS

| CN | 1859851 | 11/2006 | | |
| JP | 2002-513287 | 5/2002 | | |
| JP | 2006-521090 | 9/2006 | | |
| JP | 2008-504020 | 2/2008 | | |
| JP | 2010-508861 | 3/2010 | | |
| WO | WO 2004/006837 | 1/2004 | | |
| WO | WO-2007047764 | A2* | 4/2007 | ......... C07K 14/4748 |
| WO | WO 2012/149364 | 11/2012 | | |
| WO | WO 2014/043637 | 3/2014 | | |
| WO | WO-2014043637 | A1* | 3/2014 | ......... A61K 39/0275 |

OTHER PUBLICATIONS

Pasetti et al. 2003 (Animal models paving the way for clinical trials of attenuated *Salmonella enterica* serovar Typhi live oral vaccines and live vectors; Vaccine 21: 401-418) (Year: 2003).*
Xie et al. 2009 (Anti-tumor effects of a human VEGFR-2-based DNA vaccine in mouse models; Genetic Vaccines and Therapy 7(10): 1-10) (Year: 2009).*
U.S. Appl. No. 15/785,743, filed Oct. 17, 2017, Springer et al.
Bolhassani et al. "Therapeutic live vaccines as a potential anticancer strategy", International Jounral of Cancer, vol. 131, No. 8, Oct. 15, 2012, pp. 1733-1743, XP055079654.
Chen "User guide pVAX1™—Catalog No. V260-20", Invitrogen by Life Technologies Corporation, Mar. 2, 2012, pp. i-16, XP002713155.
Hotz et al. "Improvement of the live vaccine strain *Salmonella enterica* serovar Typhi Ty21a for antigen delivery via the hemolysin secretion system of *Escherichia coli*", International Journal of Medical Microbiology, Urban Und Fischer, DE, vol. 299, No. 2, Feb. 1, 2009 (Feb. 1, 2009), pp. 109-119.
Le et al. "A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction", Clinical Cancer Research, vol. 18, No. 3, Feb. 1, 2012 (Feb. 1, 2012), pp. 858-868.
Niethammer et al. "A DNA vaccine against VEGF receptor 2 prevents effective angiogenesis and inhibits tumor growth", Nature Medicine, vol. 8, No. 12, 2002, p. 1369-1375, XP002968984.
Niethammer et al. "Double-blind, placebo-controlled first in human study to investigate an oral vaccine aimed to elicit an immune reaction against the VEGF-Receptor 2 in patients with stage IV and locally advanced pancreatic cancer", BMC Cancer, vol. 12, Aug. 20, 2012, pp. 361-368, XP002692736.
Oka et al. "Induction of WT1 (Wilms' tumor gene)—specific cytotoxic T lymphocytes by WT1 peptide vaccine and the resultant cancer regression", Proceedings of the National Academy of Sciences—PNAS,National Academy of Sciences, US, vol. 101, No. 38, Sep. 21, 2004, pp. 13885-13890, XP002391406.

(Continued)

*Primary Examiner* — Mary Maille Lyons
(74) *Attorney, Agent, or Firm* — Sheridan Ross P.C.

(57) ABSTRACT

The present invention relates to an attenuated mutant strain of *Salmonella* comprising a recombinant DNA molecule encoding Wilms' tumor Protein I. In particular, the present invention relates to the use of said attenuated mutant strain of *Salmonella* in cancer immunotherapy.

14 Claims, 6 Drawing Sheets

Figure 3:
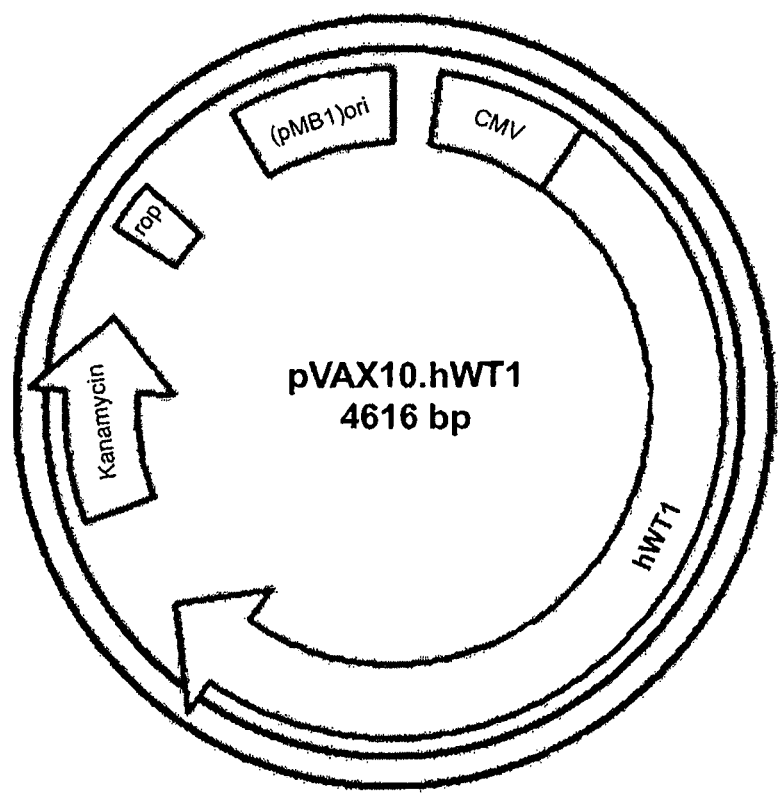

Specification includes a Sequence Listing.

(56) References Cited

OTHER PUBLICATIONS

Osada et al. "Induction of Wilms' Tumor Protein (WT1)—Specific Antitumor Immunity Using a Truncated WT1-Expressing Adenovirus Vaccine", Clinical Cancer Research, vol. 15, No. 8, Apr. 1, 2009, pp. 2789-2796, XP055079390.
Shahabi et al. "Live, attenuated strains of Listeria and Salmonella as vaccine vectors in cancer treatment", Bioengineered Bugs, vol. 1, No. 4, Jan. 1, 2010, pp. 235-239, XP055079663.
Nishikawa et al. "In vivo antigen delivery by a *Salmonella typhimurium* type III secretion system for therapeutic cancer vaccines", Journal of Clinical Investigation, vol. 116, No. 7, Jul. 1, 2006, pp. 1946-1954, XP002415290.
International Search Report and Written Opinion prepared by the European Patent Office dated Aug. 11, 2014, for International Application No. PCT/EP2014/001099, 16 pages.
Official Action for U.S. Appl. No. 14/786,652, dated Jan. 30, 2017 20 pages.
Official Action for U.S. Appl. No. 14/786,652, dated Aug. 25, 2017 19 pages.
Notice of Allowance for U.S. Appl. No. 14/786,652, dated Oct. 27, 2017 11 pages.
Xiong et al. "Novel cancer vaccine based on genes of Salmonella pathogenicity island 2," International Journal of Cancer, 2010, vol. 126, No. 11, pp. 2622-2634.
Darji et al. "Oral Somatic Transgene Vaccination Using Attenuated *S. typhimurium*," Cell, Dec. 1997, vol. 91, pp. 765-775.
Darji et al. "Oral delivery of DNA vaccines using attenuated *Salmonella typhimurium* as carrier," FEMS Immunology and Medical Microbiology, 2000, vol. 27, pp. 341-349.
Galen et al. "A Bivalent Typhoid Live Vector Vaccine Expressing both Chromosome- and Plasmid-Encoded Yersinia pestis Antigens Fully Protects against Murine Lethal Pulmonary Plague Infection," Infection and Immunity, Jan. 2015, vol. 83, No. 1, pp. 161-172.
Muhsen et al. "Helicobacter pylori Infection Affects Immune Responses Following Vaccination of Typhoid-Naïve US Adults With Attenuated *Salmonella typhi* Oral Vaccine CVD 908-htrA," The Journal of Infectious Diseases, 2014, vol. 209, pp. 1452-1458.
Stratford et al. "Optimization of *Salmonella enterica* Serovar Typhi ΔaroC ΔssaV Derivatives as Vehicles for Delivering Heterologous Antigens by Chromosomal Integration and In Vivo Inducible Promoters," Infection and Immunity, Jan. 2005, vol. 73, No. 1, pp. 362-368.

\* cited by examiner

Figure 1:

```
          10         20         30         40         50         60
MGSDVRDLNA LLPAVPSLGG GGGCALPVSG AAQWAPVLDF APPGASAYGS LGGPAPPPAP 70         80         90        100        110        120
PPPPPPPPHS FIKQEPSWGG AEPHEEQCLS AFTVHFSGQF TGTAGACRYG PFGPPPPSQA 130        140        150        160        170        180
SSGQARMFPN APYLPSCLES QPAIRNQGYS TVTFDGTPSY GHTPSHHAAQ FPNHSFKHED 190        200        210        220        230        240
PMGQQGSLGE QQYSVPPPVY GCHTPTDSCT GSQALLLRTP YSSDNLYQMT SQLECMTWNQ 250        260        270        280        290        300
MNLGATLKGV AAGSSSSVKW TEGQSNHSTG YESDNHTTPI LCGAQYRIHT HGVFRGIQDV 310        320        330        340        350        360
RRVPGVAPTL VRSASETSEK RPFMCAYPGC NKRYFKLSHL QMHSRKHTGE KPYQCDFKDC

370
ERRFSRSDQL K
```

Figure 2A:

TGGGCTTTTGCTGGCCTTTTGCTCACATGTTCTTGACTCTTCGCGATGTACGGGCC
AGATATACGCGTTGACATTGATTATTGACTAGTTATTAATAGTAATCAATTACGG
GGTCATTAGTTCATAGCCCATATATGGAGTTCCGCGTTACATAACTTACGGTAAA
TGGCCCGCCTGGCTGACCGCCCAACGACCCCGCCCATTGACGTCAATAATGACG
TATGTTCCCATAGTAACGCCAATAGGGACTTTCCATTGACGTCAATGGGTGGACT
ATTTACGGTAAACTGCCCACTTGGCAGTACATCAAGTGTATCATATGCCAAGTAC
GCCCCCTATTGACGTCAATGACGGTAAATGGCCCGCCTGGCATTATGCCCAGTAC
ATGACCTTATGGGACTTTCCTACTTGGCAGTACATCTACGTATTAGTCATCGCTAT
TACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCA
CCAAAATCAACGGGACTTTCCAAAATGTCGTAACAACTCCGCCCCATTGACGCAA
ATGGGCGGTAGGCGTGTACGGTGGGAGGTCTATATAAGCAGAGCTCTCTGGCTAA
CTAGAGAACCCACTGCTTACTGGCTTATCGAAATTAATACGACTCACTATAGGGA
GACCCAAGCTGGCTAGCATGGACTTCCTCTTGCTGCAGGACCCGGCTTCCACGTG
TGTCCCGGAGCCGGCGTCTCAGCACACGCTCCGCTCCGGGCCTGGGTGCCTACAG
CAGCCAGAGCAGCAGGGAGTCCGGGACCCGGGCGGCATCTGGGCCAAGTTAGGC
GCCGCCGAGGCCAGCGCTGAACGTCTCCAGGGCCGGAGGAGCCGCGGGGCGTCC
GGGTCTGAGCCGCAGCAAATGGGCTCCGACGTGCGGGACCTGAACGCGCTGCTG
CCCGCCGTCCCCTCCCTGGGTGGCGGCGGCGGCTGTGCCCTGCCTGTGAGCGGCG
CGGCGCAGTGGGCGCCGGTGCTGGACTTTGCGCCCCGGGCGCTTCGGCTTACGG
GTCGTTGGGCGGCCCCGCGCCGCCACCGGCTCCGCCGCCACCCCGCCGCCGCCG
CCTCACTCCTTCATCAAACAGGAGCCGAGCTGGGGCGGCGCGGAGCCGCACGAG
GAGCAGTGCCTGAGCGCCTTCACTGTCCACTTTCCGGCCAGTTCACTGGCACAG
CCGGAGCCTGTCGCTACGGGCCCTTCGGTCCTCCTCCGCCCAGCCAGGCGTCATC
CGGCCAGGCCAGGATGTTTCCTAACGCGCCCTACCTGCCCAGCTGCCTGGAGAGC
CAGCCCGCTATTCGCAATCAGGGTTACAGCACGGTCACCTTCGACGGGACGCCCA
GCTACGGTCACACGCCCTCGCACCATGCGGCGCAGTTCCCCAACCACTCATTCAA
GCATGAGGATCCCATGGGCCAGCAGGGCTCGCTGGGTGAGCAGCAGTACTCGGT
GCCGCCCCGGTCTATGGCTGCCACACCCCCACCGACAGCTGCACCGGCAGCCAG
GCTTTGCTGCTGAGGACGCCCTACAGCAGTGACAATTTATACCAAATGACATCCC
AGCTTGAATGCATGACCTGGAATCAGATGAACTTAGGAGCCACCTTAAAGGGAG
TTGCTGCTGGGAGCTCCAGCTCAGTGAAATGGACAGAAGGGCAGAGCAACCACA
GCACAGGGTACGAGAGCGATAACCACACAACGCCCATCCTCTGCGGAGCCCAAT
ACAGAATACACACGCACGGTGTCTTCAGAGGCATTCAGTGACTCGAGTCTAGAGG
GCCCGTTTAAACCCGCTGATCAGCCTCGACTGTGCCTTCTAGTTGCCAGCCATCTG
TTGTTTGCCCCTCCCCCGTGCCTTCCTTGACCCTGGAAGGTGCCACTCCCACTGTC
CTTTCCTAATAAAATGAGGAAATTGCATCGCATTGTCTGAGTAGGTGTCATTCTAT
TCTGGGGGGTGGGGTGGGCAGGACAGCAAGGGGGAGGATTGGGAAGACAATA
GCAGGCATGCTGGGGATGCGGTGGGCTCTATGGCTTCTACTGGGCGGTTTTATGG
ACAGCAAGCGAACCGGAATTGCCAGCTGGGGCGCCCTCTGGTAAGGTTGGGAAG
CCCTGCAAAGTAAACTGGATGGCTTTCTCGCCGCCAAGGATCTGATGGCGCAGGG
GATCAAGCTCTGATCAAGAGACAGGATGAGGATCGTTTCGCATGATTGAACAAG
ATGGATTGCACGCAGGTTCTCCGGCCGCTTGGGTGGAGAGGCTATTCGGCTATGA
CTGGGCACAACAGACAATCGGCTGCTCTGATGCCGCCGTGTTCCGGCTGTCAGCG
CAGGGGCGCCCGGTTCTTTTTGTCAAGACCGACCTGTCCGGTGCCCTGAATGAAC
TGCAAGACGAGGCAGCGCGGCTATCGTGGCTGGCCACGACGGGCGTTCCTTGCGC
AGCTGTGCTCGACGTTGTCACTGAAGCGGGAAGGGACTGGCTGCTATTGGGCGAA

Figure 2B:

GTGCCGGGGCAGGATCTCCTGTCATCTCACCTTGCTCCTGCCGAGAAAGTATCCA
TCATGGCTGATGCAATGCGGCGGCTGCATACGCTTGATCCGGCTACCTGCCCATT
CGACCACCAAGCGAAACATCGCATCGAGCGAGCACGTACTCGGATGGAAGCCGG
TCTTGTCGATCAGGATGATCTGGACGAAGAGCATCAGGGGCTCGCGCCAGCCGA
ACTGTTCGCCAGGCTCAAGGCGAGCATGCCCGACGGCGAGGATCTCGTCGTGACC
CATGGCGATGCCTGCTTGCCGAATATCATGGTGGAAAATGGCCGCTTTTCTGGAT
TCATCGACTGTGGCCGGCTGGGTGTGGCGGACCGCTATCAGGACATAGCGTTGGC
TACCCGTGATATTGCTGAAGAGCTTGGCGGCGAATGGGCTGACCGCTTCCTCGTG
CTTTACGGTATCGCCGCTCCCGATTCGCAGCGCATCGCCTTCTATCGCCTTCTTGA
CGAGTTCTTCTGAATTATTAACGCTTACAATTTCCTGATGCGGTATTTTCTCCTTAC
GCATCTGTGCGGTATTTCACACCGCATACAGGTGGCACTTTTCGGGGAAATGTGC
GCGGAACCCCTATTTGTTTATTTTTCTAAATACATTCAAATATGTATCCGCTCATG
AGACAATAACCCTGATAAATGCTTCAATAATAGCACGTGCTAAAACTTCATTTTT
AATTTAAAAGGATCTAGGTGAAGATCCTTTTGATAATCTCATGACCAAAATCCC
TTAACGTGAGTTTTCGTTCCACTGAGCGTCAGACCCCATCAGTGACCAAACAGG
AAAAAACCGCCCTTAACATGGCCCGCTTTATCAGAAGCCAGACATTAACGCTTCT
GGAGAAACTCAACGAGCTGGACGCGGATGAACAGGCAGACATCTGTGAATCGCT
TCACGACCACGCTGATGAGCTTTACCGCAGCTGCCTCGCGCGTTTCGGTGATGAC
GGTGAAAACCTCTGACACATGCAGCTCCCGGAGACGGTCACAGCTTGTCTGTAAG
CGGATGCCGGGAGCAGACAAGCCCGTCAGGGCGCGTCAGCGGGTGTTGGCGGGT
GTCGGGGCGCAGCCATGACCCAGTCACGTAGCGATAGCGGAGTGTATACTGGCTT
AACTATGCGGCATCAGAGCAGATTGTACTGAGAGTGCACCATATGCGGTGTGAA
ATACCGCACAGATGCGTAAGGAGAAAATACCGCATCAGGCGCTCTTCCGCTTCCT
CGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCA
AGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTC
CGCCTTTCTCCCTTCGGGAAGCGTGGCGCTTTCTCATAGCTCACGCTGTAGGTATC
TCAGTTCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTACA
CTAGAAGGACAGTATTTGGTATCTGCGCTCTGCTGAAGCCAGTTACCTTCGGAAA
AAGAGTTGGTAGCTCTTGATCCGGCAAACAAACCACCGCTGGTAGCGGTGGTTTT
TTTGTTTGCAAGCAGCAGATTACGCGCAGAAAAAAGGATCTCAAGAAGATCCTT
TGATC

SALMONELLA-BASED VECTORS FOR CANCER IMMUNOTHERAPY TARGETING WILMS' TUMOR GENE WT1

CROSS REFERENCE TO RELATED APPLICATIONS

This application is a continuation of U.S. patent application Ser. No. 14/786,652, filed Oct. 23, 2015, which is a national stage application under 35 U.S.C. 371 and claims the benefit of PCT Application No. PCT/EP2014/001099 having an international filing date of 24 Apr. 2014, which designated the United States, which PCT application claimed the benefit of European Patent Application No. 13002245.2 filed Apr. 25, 2013, the disclosure of each of which are incorporated herein by reference.

REFERENCE TO A SEQUENCE LISTING

The content of the ASCII text file of the sequence listing named "2014018233 Sequence_Listing.txt" which is 10 kb in size was created on Apr. 24, 2014 and electronically submitted via EFS-Web with the application; it is incorporated herein by reference in its entirety.

FIELD OF THE INVENTION

The present invention relates to an attenuated mutant strain of Salmonella comprising a recombinant DNA molecule encoding Wilms' tumor Protein 1. In particular, the present invention relates to the use of said attenuated mutant strain of Salmonella in cancer immunotherapy.

BACKGROUND OF THE INVENTION

Wilms' tumor gene 1 (WT1) encodes a zinc finger transcription factor involved in cell proliferation and differentiation. It is highly expressed in a wide variety of malignancies including several types of hematological malignancies and various solid tumors. In contrast, normal tissue expression of WT1 in adults is restricted to gonads, uterus, kidney, mesothelium and $CD34^+$ progenitor cells in various types of tissues. WT1 was originally proposed as a tumor suppressor gene. However, more recent evidence points to oncogenic functions of this transcription factor; Wt-1 negatively affects differentiation and promotes proliferation of progenitor cells. Furthermore, overexpressed WT1 is immunogenic; WT1 specific T cells as well as IgG anti-WT1 antibodies have been observed in cancer patients. Thus, WT-1 is a promising candidate for the development of cancer vaccines.

Human clinical trials with WT1 vaccines based on HLA (human leukocyte antigen)-restricted WT1 peptide fragments have been reported. Osada et al., Clin Cancer Res 2009; 15:2789-2796, discloses a WT1-encoding Adenovirus Vaccine.

To the inventor's knowledge, no live bacterial cancer vaccine targeting WT1 has been reported. Furthermore, no oral cancer vaccine targeting WT1 has been described.

Attenuated derivatives of Salmonella enterica are attractive vehicles for the delivery of heterologous antigens to the mammalian immune system, since S. enterica strains can potentially be delivered via mucosal routes of immunization, i.e. orally or nasally, which offers advantages of simplicity and safety compared to parenteral administration. Furthermore, Salmonella strains elicit strong humoral and cellular immune responses at the level of both systemic and mucosal compartments. Batch preparation costs are relatively low and formulations of live bacterial vaccines are highly stable. Attenuation can be accomplished by deletion of various genes, including virulence, regulatory, and metabolic genes.

Several Salmonella typhimurium strains attenuated by aro mutations have been shown to be safe and effective delivery vehicles for heterologous antigens in animal models.

Approaches of delivering DNA constructs encoding antigens, in particular VEGF receptor proteins, via live attenuated Salmonella typhimurium strains into mouse target cells are described in WO 03/073995. Niethammer et al., (Nature Medicine 2002, 8(12), 1369) demonstrated that the attenuated S. typhimurium aroA strain SL7207 harboring an expression vector encoding the murine vascular endothelial growth factor receptor 2 (VEGFR-2 or FLK-1), which is essential for tumor angiogenesis, is functional as a cancer vaccine.

There is however only one attenuated Salmonella enterica serovar strain, namely Salmonella enterica serovar typhi Ty21a (short: S. typhi Ty21a), which has been accepted for use in humans and is distributed under the trade name of Vivotif® (Berna Biotech Ltd., a Crucell Company, Switzerland; marketing authorization number PL 15747/0001 dated 16 Dec. 1996).

This well-tolerated, live oral vaccine against typhoid fever was derived by chemical mutagenesis of the wild-type virulent bacterial isolate S. typhi Ty2 and harbors a loss-of-function mutation in the galE gene, as well as other less defined mutations. It has been licensed as typhoid vaccine in many countries after it was shown to be efficacious and safe in field trials.

WT1 is a promising tumor antigen for the development of cancer vaccines. Major limitations of previously available WT1 peptide vaccines are HLA-restriction and parenteral administration. The great need for improved cancer therapy approaches based on targeting WT1 has not been met so far.

OBJECTS OF THE INVENTION

In view of the prior art, it is an object of the present invention to provide a novel oral WT1 targeting cancer vaccine. Such a WT1 targeting cancer vaccine would offer major advantages for improving the treatment options for cancer patients.

SUMMARY OF THE INVENTION

In one aspect, the present invention relates to an attenuated mutant strain of Salmonella comprising at least one copy of a recombinant DNA molecule comprising an expression cassette encoding Wilms' Tumor Protein (WT1).

The attenuated Salmonella strain of the present invention was shown to exhibit antitumor activity in a mouse model challenged with murine leukemia cells. To the inventor's knowledge, this novel attenuated Salmonella strain is the first live bacterial cancer vaccine targeting WT1. In addition, the attenuated. Salmonella strain of the present invention is the first oral cancer vaccine targeting WT1. Since WT1 is overexpressed in a wide variety of hematological malignancies and solid tumor, the attenuated Salmonella strain of the present invention has great potential as universal cancer vaccine.

In a first study, the vaccine according to the present invention (VXM06) has been demonstrated to efficiently prolong survival of mice bearing intraperitoneally implanted leukemia cells. These results indicate that vaccination with VXM06 may lead to an immune response and the development of an immune memory against tumor cells overexpressing WT1. It is remarkable and surprising that the novel vaccine VXM06 is effective at relatively low doses. The attenuated Salmonella mutant strain of the present invention may be applied in monotherapy or in combination with a second attenuated mutant strain of Salmonella comprising a DNA molecule encoding a second tumor antigen. Furthermore, the attenuated mutant strain of the present invention may be administered in combination with chemotherapy, radiotherapy or biological cancer therapy. Treatment with VXM06 may also be effective, if the patient has developed a resistance to chemotherapy (chemo-refractory patients). The novel attenuated Salmonella strain of the present invention might therefore be useful in novel, greatly improved cancer therapy approaches.

In particular embodiments, the attenuated mutant strain of Salmonella is of the species Salmonella enterica. In particular embodiments, the attenuated mutant strain of Salmonella is Salmonella typhi Ty21a.

In particular embodiments, the expression cassette is a eukaryotic expression cassette.

In particular embodiments, WT1 is selected from the group consisting of human WT1 and a protein that shares at least about 80% sequence identity therewith.

In particular embodiments, WT1 is truncated. In particular embodiments, the zinc finger domain of WT1 is deleted. In particular embodiments, the truncated WT1 has the amino acid sequence as found in SEQ ID NO 1.

In particular embodiments, the recombinant DNA molecule comprises the kanamycin antibiotic resistance gene, the pMB1 ori, and a eukaryotic expression cassette encoding human WT1 or a protein that shares at least 80% sequence identity therewith, particularly truncated human WT1, under the control of a CMV promoter. In particular embodiments, the recombinant DNA molecule is a plasmid designated pVAX10.hWT1 and has the nucleic acid sequence as found in SEQ ID NO 2.

In particular embodiments, the attenuated mutant strain of Salmonella is for use as a medicament.

In particular embodiments, the attenuated mutant strain of Salmonella is for use as a vaccine.

In particular embodiments, the attenuated mutant strain of Salmonella is for use in cancer immunotherapy.

In particular embodiments, cancer immunotherapy further comprises administration of one or more further attenuated mutant strain(s) of Salmonella comprising at least one copy of a recombinant DNA molecule comprising an expression cassette encoding a tumor antigen and/or a tumor stroma antigen. In particular embodiments, said one or more further attenuated mutant strain(s) of Salmonella is/are Salmonella typhi Ty21a comprising a eukaryotic expression cassette. In particular embodiments, said one or more further strain(s) of Salmonella comprise(s) an attenuated mutant strain(s) of Salmonella encoding human VEGFR-2.

In particular embodiments, the attenuated mutant strain of Salmonella is co-administered with said one or more further attenuated mutant strain(s) of Salmonella.

In particular embodiments, cancer immunotherapy is accompanied by chemotherapy, radiotherapy or biological cancer therapy.

In particular embodiments, the attenuated mutant strain of Salmonella is administered during the chemotherapy or the radiotherapy treatment cycle or during biological cancer therapy.

In particular embodiments, the attenuated mutant strain of Salmonella is administered before the chemotherapy or the radiotherapy treatment cycle or before biological cancer therapy.

In particular embodiments, the attenuated mutant strain of Salmonella is administered after the chemotherapy or the radiotherapy treatment cycle or after biological cancer therapy.

In further embodiments the attenuated mutant strain of Salmonella is administered before and during at least one of the chemotherapy, the radiotherapy treatment cycle and the biological cancer therapy. In cases where more than one of the chemotherapy, the radiotherapy and the biological cancer therapy are carried out the attenuated mutant strain of Salmonella may be administered before or during or before and during at least one of these therapies, particularly during at least two of these therapies.

In particular embodiments, the attenuated mutant strain of Salmonella is administered orally.

In particular embodiments, the cancer is selected from leukemia, particularly from acute myeloid leukemia (AML) and acute lymphoid leukemia (ALL), and from solid tumors, particularly from lung cancer, breast cancer, esophageal, colon, colorectal, gastric, cholangioductal, pancreatic cancer, glioblastoma, head and neck cancer, synovial sarcoma, angiosarcoma, osteosarcoma, thyroid cancer, cervical, endometrial, ovarian cancer, neuroblastoma, rhabdomyosarcoma, prostate cancer.

In particular embodiments, the single dose is from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU).

In particular embodiments, the attenuated mutant strain of Salmonella is for use in personalized cancer immunotherapy comprising the step of assessing the tumor antigen expression pattern and/or stroma antigen expression pattern of a patient.

DETAILED DESCRIPTION OF THE INVENTION

The present invention may be understood more readily by reference to the following detailed description of the invention and the examples included therein.

In one aspect, the present invention relates to an attenuated mutant strain of Salmonella comprising at least one copy of a recombinant DNA molecule comprising an expression cassette encoding Wilms' Tumor Protein (WT1).

According to the invention, the attenuated Salmonella strain functions as the bacterial carrier of the recombinant DNA molecule comprising an expression cassette encoding Wilms' Tumor Protein (WT1) for the delivery of said recombinant DNA molecule into a target cell.

In the context of the present invention, the term "attenuated" refers to a bacterial strain of reduced virulence compared to the parental bacterial strain, not harboring the attenuating mutation. Attenuated bacterial strains have preferably lost their virulence but retained their ability to induce protective immunity. Attenuation can be accomplished by deletion of various genes, including virulence, regulatory, and metabolic genes. Attenuated bacteria may be found naturally or they may be produced artificially in the laboratory, for example by adaptation to a new medium or cell culture or they may be produced by recombinant DNA technology.

In the context of the present invention, the term "mutant strain" refers to a bacterial strain harboring a mutation in its genome. In this context, the term "mutation" refers to a change in a nucleic acid sequence, including point mutations, insertions, deletions, translocations and inversions.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

In the context of the present invention, the term "recombinant DNA molecule" refers to an engineered DNA construct, preferably composed of DNA pieces of different origin. The recombinant DNA molecule can be a linear nucleic acid, or preferably, a circular recombinant DNA plasmid generated by introducing an open reading frame encoding WT1 into an expression vector plasmid.

In the context of the present invention, the term "expression cassette" refers to a nucleic acid unit comprising at least the WT1 gene under the control of regulatory sequences controlling its expression. The expression cassette comprised in the attenuated mutant strain of Salmonella can preferably mediate transcription of the included open reading frame encoding WT1 in a target cell. Expression cassettes typically comprise a promoter, at least one open reading frame and a transcription termination signal.

The zinc finger transcription factor Wilms' tumor protein 1 is encoded by the WT1 gene. It contains four zinc finger motifs at the C-terminus and a proline/glutamine-rich DNA-binding domain at the N-terminus. Multiple transcript variants, resulting from alternative splicing at two coding exons, have been well characterized. WT1 plays an essential role in the development of the urogenital system and is involved in cell proliferation and differentiation. The WT1 gene was isolated as the gene responsible for a childhood renal neoplasm, Wilms' tumor. It is highly expressed in a wide variety of malignancies including several types of hematological malignancies and various solid tumors. In contrast, normal tissue expression of WT1 in adults is restricted to gonads, uterus, kidney, mesothelium and progenitor cells in various types of tissues. Due to its expression profile, its oncogenic functions and its immunogenic potential, the tumor antigen WT1 is a promising candidate for the development of cancer vaccines.

In particular embodiments, the attenuated mutant strain of Salmonella is of the species Salmonella enterica. In particular embodiments, the attenuated mutant strain of Salmonella is Salmonella typhi Ty21a. The attenuated S. typhi Ty21a strain is the active component of Typhoral L®, also known as Vivotif® (manufactured by Berna Biotech Ltd., a Crucell Company, Switzerland). It is currently the only licensed live oral vaccine against typhoid fever. This vaccine has been extensively tested and has proved to be safe regarding patient toxicity as well as transmission to third parties (Wandan et al., J. Infectious Diseases 1982, 145:292-295). The vaccine is licensed in more than 40 countries. The Marketing Authorization number of Typhoral L® is PL 15747/0001 dated 16 Dec. 1996. One dose of vaccine contains at least $2 \times 10^9$ viable S. typhi Ty21a colony forming units and at least $5 \times 10^9$ non-viable S. typhi Ty21a cells.

One of the biochemical properties of the Salmonella typhi Ty21a bacterial strain is its inability to metabolize galactose. The attenuated bacterial strain is also not able to reduce sulfate to sulfide which differentiates it from the wild-type Salmonella typhi Ty2 strain. With regard to its serological characteristics, the Salmonella typhi Ty21a strain contains the O9-antigen which is a polysaccharide of the outer membrane of the bacteria and lacks the O5-antigen which is in turn a characteristic component of Salmonella typhimurium. This serological characteristic supports the rationale for including the respective test in a panel of identity tests for batch release.

In particular embodiments, the expression cassette is a eukaryotic expression cassette. In the context of the present invention, the term "eukaryotic expression cassette" refers to an expression cassette which allows for expression of the open reading frame in a eukaryotic cell. It has been shown that the amount of heterologous antigen required to induce an adequate immune response may be toxic for the bacterium and result in cell death, over-attenuation or loss of expression of the heterologous antigen. Using a eukaryotic expression cassette that is not expressed in the bacterial vector but only in the target cell may overcome this toxicity problem and the protein expressed may exhibit a eukaryotic glycosylation pattern.

A eukaryotic expression cassette comprises regulatory sequences that are able to control the expression of an open reading frame in a eukaryotic cell, preferably a promoter and a polyadenylation signal. Promoters and polyadenylation signals included in the recombinant DNA molecules comprised by the attenuated mutant strain of Salmonella of the present invention are preferably selected to be functional within the cells of the subject to be immunized. Examples of suitable promoters, especially for the production of a DNA vaccine for humans, include but are not limited to promoters from Cytomegalovirus (CMV), such as the strong CMV immediate early promoter, Simian Virus 40 (SV40), Mouse Mammary Tumor Virus (MMTV), Human Immunodeficiency Virus (HIV), such as the HIV Long Terminal Repeat (LTR) promoter, Moloney virus, Epstein Barr Virus (EBV), and from Rous Sarcoma Virus (RSV) as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals. In a particular embodiment, the eukaryotic expression cassette included in the recombinant DNA molecule comprised by the attenuated mutant strain of Salmonella of the present invention comprises the BGH polyadenylation site.

In addition to the regulatory elements required for expression of the heterologous WT1 gene, like a promoter and a polyadenylation signal, other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

In particular embodiments, WT1 is selected from the group consisting of human WT1 and a protein that shares at least about 80% sequence identity therewith.

In this context, the term "about" or "approximately" means within 80% to 120%, alternatively within 90% to 110%, including within 95% to 105% of a given value or range.

In the context of the present invention, the term "protein that shares at least about 80% sequence identity with human WT1" refers to a protein that differs in the amino acid sequence and/or the nucleic acid sequence encoding the amino acid sequence of human WT1. The protein may be of natural origin, e.g. a homolog of WT1 of a different species, or an engineered protein, e.g. an engineered WT1 derivative. It is known that the usage of codons is different between species. Thus, when expressing a heterologous protein in a target cell, it may be necessary, or at least helpful, to adapt the nucleic acid sequence to the codon usage of the target cell. Methods for designing and constructing derivatives of a given protein are well known to anyone of ordinary skill in the art.

The protein that shares at least about 80% sequence identity with human WT1 may contain one or more mutations comprising an addition, a deletion and/or a substitution of one or more amino acids. According to the teaching of the present invention, said deleted, added and/or substituted amino acids may be consecutive amino acids or may be interspersed over the length of the amino acid sequence of the protein that shares at least about 80% sequence identity with human WT1. According to the teaching of the present invention, any number of amino acids may be added, deleted, and/or substitutes, as long as the sequence identity with human WT1 is at least about 80%. In particular embodiments, the sequence identity with human WT1 is at least about 80%, at least about 85%, at least about 90%, or most particularly at least about 95%. Methods and algorithms for determining sequence identity including the comparison of a parental protein and its derivative having deletions, additions and/or substitutions relative to a parental sequence, are well known to the practitioner of ordinary skill in the art. On the DNA level, the nucleic acid sequences encoding the protein that shares at least about 80% sequence identity with human WT1 may differ to a larger extent due to the degeneracy of the genetic code.

In particular embodiments, WT1 is truncated. In particular embodiments, the zinc finger domain of WT1 is deleted. In particular embodiments, the truncated WT1 has the amino acid sequence as found in SEQ ID NO 1.

The zinc finger domain at the C-terminus of WT1 comprises four zinc finger motifs. Truncated WT1 of the amino acid sequence as found in SEQ ID NO 1 represents amino acids 1 to 371 of UniProt ref P19544-7. Deletion of the zinc finger domain minimizes the risk of immunological cross reactivity with other zinc finger containing transcription factors. Furthermore, truncated WT1 lacking the zinc finger domain has greater immunogenic potential than full-length WT1. In addition, deletion of the zinc finger motifs, which are essential for DNA binding, abrogates the oncogenic potential of WT1, thus minimizing the risk of oncogenesis.

In particular embodiments, the recombinant DNA molecule comprises the kanamycin antibiotic resistance gene, the pMB1 ori, and a eukaryotic expression cassette encoding human WT1 or a protein that shares at least 80% sequence identity therewith, particularly truncated human WT1, under the control of a CMV promoter. In particular embodiments, the recombinant DNA molecule is a plasmid designated pVAX10.hWT1 and has the nucleic acid sequence as found in SEQ ID NO 2.

In particular embodiments, the recombinant DNA molecule is derived from commercially available pVAX1™ expression plasmid (Invitrogen, San Diego, Calif.). This expression vector was modified by replacing the high copy pUC origin of replication by the low copy pMB1 origin of replication of pBR322. The low copy modification was made in order to reduce the metabolic burden and to render the construct more stable. The generated expression vector backbone was designated pVAX10. Inserting human, truncated WT1 into this expression vector backbone via NheI/XhoI yielded the expression plasmid pVAX10.hWT1 having the nucleic acid sequence as found in SEQ ID NO 2. The expression plasmid pVAX10.hWT1 is schematically depicted in FIG. 3.

In particular embodiments, the attenuated mutant strain of Salmonella is for use as a medicament.

In particular embodiments, the attenuated mutant strain of Salmonella is for use as a vaccine.

In the context of the present invention, the term "vaccine" refers to an agent which is able to induce an immune response in a subject upon administration. A vaccine can preferably prevent, ameliorate or treat a disease. A vaccine in accordance with the present invention comprises an attenuated mutant strain of Salmonella, preferably S. typhi Ty21a. The vaccine in accordance with the present invention further comprises at least one copy of a recombinant DNA molecule comprising an expression cassette, preferably a eukaryotic expression cassette, encoding WT1, preferably selected from human WT1 or a protein that shares at least about 80% sequence identity therewith. Preferably, said WT1 is truncated, particularly the zinc finger domain is deleted.

The live attenuated Salmonella mutant strain according to the present invention comprising a recombinant DNA molecule encoding WT1 can be used as a vehicle for the oral delivery of this recombinant DNA molecule. Such a delivery vector comprising a DNA molecule encoding a heterologous antigen, such as WT1, is termed DNA vaccine.

Genetic immunization might be advantageous over conventional vaccination. The target DNA can be detected for a considerable period of time thus acting as a depot of the antigen. Sequence motifs in some plasmids, like GpC islands, are immunostimulatory and can function as adjuvants furthered by the immunostimulation due to LPS and other bacterial components.

In contrast to peptide vaccines that can only mediate immunity against a small fragment of the WT1 protein, genetic vaccination may result in immunity against a wide variety of epitopes present over the whole length of the encoded WT1 protein.

Apart from that, WT1 peptide vaccine, which have been used in clinical trials for the most part, have limited application due to HLA restriction of the peptides, i.e. their binding capacity to HLA molecules of antigen presenting cells (APCs). In contrast, the DNA vaccine of the present invention is not HLA restricted.

Live bacterial vectors produce their own immunomodulatory factors such as lipopolysaccharides (LPS) in situ which may constitute an advantage over other forms of administration such as microencapsulation. Moreover, the use of the natural route of entry proves to be of benefit since many bacteria, like Salmonella, egress from the gut lumen via the M cells of Peyer's patches and migrate eventually into the lymph nodes and spleen, thus allowing targeting of vaccines to inductive sites of the immune system. The vaccine strain of *Salmonella typhi*, Ty21a, has been demonstrated to-date to have an excellent safety profile. Upon exit from the gut lumen via the M cells, the bacteria are taken up by phagocytic cells, such as macrophages and dendritic cells. These cells are activated by the pathogen and start to differentiate, and probably migrate into the lymph nodes and spleen. Due to their attenuating mutations, bacteria of the *S. typhi* Ty21 strain are not able to persist in these phagocytic cells but die at this time point. The recombinant DNA molecules are released and subsequently transferred into the cytosol of the phagocytic immune cells, either via a specific transport system or by endosomal leakage. Finally, the recombinant DNA molecules enter the nucleus, where they are transcribed, leading to WT1 expression in the cytosol of the phagocytic cells. Specific cytotoxic T cells against WT1 are induced by the activated antigen presenting cells.

There is no data available to-date indicating that *S. typhi* Ty21a is able to enter the bloodstream systemically. The live attenuated *Salmonella typhi* Ty21a vaccine strain thus allows specific targeting of the immune system while exhibiting an excellent safety profile.

Attenuated derivatives of *Salmonella enterica* are attractive as vehicles for the delivery of heterologous antigens to the mammalian immune system because *S. enterica* strains can potentially be delivered via mucosal routes of immunization, i.e. orally or nasally, which offers advantages of simplicity and safety compared to parenteral administration. Furthermore, *Salmonella* strains elicit strong humoral and cellular immune responses at the level of both systemic and mucosal compartments.

In particular embodiments, the attenuated mutant strain of *Salmonella* is for use in cancer immunotherapy.

In particular embodiments, cancer immunotherapy further comprises administration of one or more further attenuated mutant strain(s) of *Salmonella* comprising at least one copy of a recombinant DNA molecule comprising an expression cassette encoding a tumor antigen and/or a tumor stroma antigen. In particular embodiments, said one or more further mutant strain(s) of *Salmonella* is/are *Salmonella typhi* Ty21a comprising a eukaryotic expression cassette. In particular embodiments, said one or more further strain(s) of *Salmonella* comprise(s) an attenuated mutant strain of *Salmonella* encoding human VEGFR-2.

Combining the attenuated mutant strain of *Salmonella* of the present invention with a second attenuated mutant strain comprising a DNA molecule encoding a second tumor antigen may have synergistic antitumor effects. In particular, simultaneous targeting of different tumor antigens may minimize the risk of tumor escape. Combining WT1 based cancer immunotherapy with VEGFR-2 based immunotherapy may prove especially effective, since WT1 overexpressing tumor cells and the tumor vasculature are attacked at the same time.

In particular embodiments, the attenuated mutant strain of *Salmonella* is co-administered with said one or more further attenuated mutant strain(s) of *Salmonella*.

In the context of the present invention, the term "co-administration" or "co-administer" means administration of two different attenuated mutant strains of *Salmonella* within three consecutive days, more particularly within two consecutive days, more particularly on the same day, more particularly within 12 hours. Most particularly, in the context of the present invention, the term "co-administration" refers to simultaneous administration of two different attenuated mutant strains of *Salmonella*.

In particular embodiments, cancer immunotherapy is accompanied by chemotherapy, radiotherapy or biological cancer therapy. For cure of cancer, complete eradication of cancer stem cells may be essential. For maximal efficacy, a combination of different therapy approaches may be beneficial.

In the context of the present invention, the term "biological cancer therapy" or "cancer immunotherapy" refers to the stimulation of the patient's immune system to attack malignant tumor cells or the tumor stroma. Biological cancer therapy approaches include delivery of tumor antigens, delivery of therapeutic antibodies as drugs, administration of immunostimulatory cytokines and administration of immune cells.

Chemotherapeutic agents that may be used in combination with the attenuated mutant strain of *Salmonella* of the present invention may be, for example: gemcitabine, amifostine (ethyol), cabazitaxel, cisplatin, dacarbazine (DTIC), dactinomycin, docetaxel, mechlorethamine, streptozocin, cyclophosphamide, carmustine (BCNU), lomustine (CCNU), doxorubicin (adriamycin), doxorubicin lipo (doxil), folinic acid, gemcitabine (gemzar), daunorubicin, daunorubicin lipo (daunoxome), procarbazine, ketokonazole, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, oxaliplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof.

Most preferred chemotherapeutic agents according to the invention in combination with VXM06 are cabazitaxel, carboplatin, oxaliplatin, cisplatin, cyclophosphamide, docetaxel, gemcitabine, doxorubicin, paclitaxel (taxol), irinotecan, vincristine, vinblastine, vinorelbin, folinic acid, 5-fluorouracil and bleomycin, especially gemcitabine.

It may be also favorable dependent on the occurrence of possible side effects, to include treatment with antibiotics or anti-inflammatory agents.

Should adverse events occur that resemble hypersensitivity reactions mediated by histamine, leukotrienes, or cytokines, treatment options for fever, anaphylaxis, blood pressure instability, bronchospasm, and dyspnoea are available. Treatment options in case of unwanted T-cell derived auto-aggression are derived from standard treatment schemes in acute and chronic graft vs. host disease applied after stem cell transplantation. Cyclosporin and glucocorticoids are proposed as treatment options.

In the unlikely case of systemic *Salmonella typhi* Ty21a type infection, appropriate antibiotic therapy is recommended, for example with fluoroquinolones including ciprofloxacin or ofloxacin. Bacterial infections of the gastrointestinal tract are to be treated with respective agents, such as rifaximin.

In particular embodiments, the attenuated mutant strain of *Salmonella* is administered during the chemotherapy or the radiotherapy treatment cycle or during biological cancer therapy.

In particular embodiments, the attenuated mutant strain of *Salmonella* is administered before the chemotherapy or the radiotherapy treatment cycle or before biological cancer therapy. This approach may have the advantage that chemotherapy or radiotherapy can be performed under conditions of enhanced cancer immunity.

In particular embodiments, the attenuated mutant strain of *Salmonella* is administered after the chemotherapy or the radiotherapy treatment cycle or after biological cancer therapy.

In particular embodiments, the attenuated mutant strain of *Salmonella* is administered orally. Oral administration is simpler, safer and more comfortable than parenteral administration. WT1 peptide vaccines, which have been used in clinical trials for the most part, are usually administered subcutaneously or intradermally, often resulting in skin erythema and local inflammation reactions. These adverse effects may be overcome by oral administration of the DNA vaccine of the present invention. The attenuated mutant strain of *Salmonella* of the present invention may however also be administered by any other suitable route. Preferably, a therapeutically effective dose is administered to the subject, and this dose depends on the particular application, the type of malignancy, the subject's weight, age, sex and state of health, the manner of administration and the formulation, etc. Administration may be single or multiple, as required.

The attenuated mutant strain of *Salmonella* of the present invention may be provided in the form of a solution, a suspension, lyophilisate, or any other suitable form. It may be provided in combination with pharmaceutically acceptable carriers, diluents, and/or excipients. Agents for adjusting the pH value, buffers, agents for adjusting toxicity, and the like may also be included. In the context of the present invention, the term "pharmaceutically acceptable" refers to molecular entities and other ingredients of pharmaceutical compositions that are physiologically tolerable and do not typically produce untoward reactions when administered to a mammal (e.g., human). The term "pharmaceutically acceptable" may also mean approved by a regulatory agency of a Federal or a state government or listed in the U.S. Pharmacopeia or other generally recognized pharmacopeia for use in mammals, and, more particularly, in humans.

In particular embodiments, the cancer is selected from leukemia, particularly from acute myeloid leukemia (AML) and acute lymphoid leukemia (ALL), and from solid tumors, particularly from lung cancer, breast cancer, esophageal, colon, colorectal, gastric, cholangioductal, pancreatic cancer, glioblastoma, head and neck cancer, synovial sarcoma, angiosarcoma, osteosarcoma, thyroid cancer, cervical, endometrial, ovarian cancer, neuroblastoma, rhabdomyosarcoma, prostate cancer.

The vaccine of the present invention is surprisingly effective at relatively low doses. In particular embodiments, the single dose is from about $10^5$ to about $10^{11}$, particularly from about $10^6$ to about $10^{10}$, more particularly from about $10^6$ to about $10^9$, more particularly from about $10^6$ to about $10^8$, most particularly from about $10^6$ to about $10^7$ colony forming units (CFU). Administration of low doses of this live bacterial vaccine minimizes the risk of excretion and thus of transmission to third parties.

In this context, the term "about" or "approximately" means within a factor of 3, alternatively within a factor of 2, including within a factor of 1.5 of a given value or range.

In particular embodiments, the attenuated mutant strain of *Salmonella* is for use in individualized cancer immunotherapy comprising the step of assessing the tumor antigen expression pattern and/or stroma antigen expression pattern of a patient.

VXM06 can be used—either by itself or in combination with other *Salmonella typhi* Ty21a based cancer vaccines comprising eukaryotic expression systems—for the treatment of various cancer types. In particular embodiments, VXM06 may be used for individualized patient specific cancer treatment. For that purpose, the patient's tumor and/or stromal antigen expression pattern may be assessed in a first step for example by companion diagnostics targeting the patient's specific tumor and/or stromal antigen pattern. Depending on the patient's tumor and/or stromal antigen expression pattern VMX06 may be administered either alone or in combination with one or more suitable further *Salmonella typhi* Ty21a based cancer vaccine(s) comprising eukaryotic expression systems. Combinations of VXM06 with one or more further *Salmonella typhi* Ty21a based cancer vaccine(s) may however also be administered as fixed combinations. These cocktails combining two or more *Salmonella typhi* Ty21a based cancer vaccines can be composed from separate off the shelf products. The combinations, either fixed or individualized may contain VXM01 as anti-angiogenic basis therapy.

SHORT DESCRIPTION OF FIGURES AND TABLES

FIG. 1: Amino acid sequence of truncated human WT1 encoded by WT1 cDNA contained in plasmid pVAX10.hWT1

FIGS. 2A and 2B: Nucleic acid sequence of pVAX10.hWT1

FIG. 3: Plasmid map of pVAX10.hWT1

Figure 4:
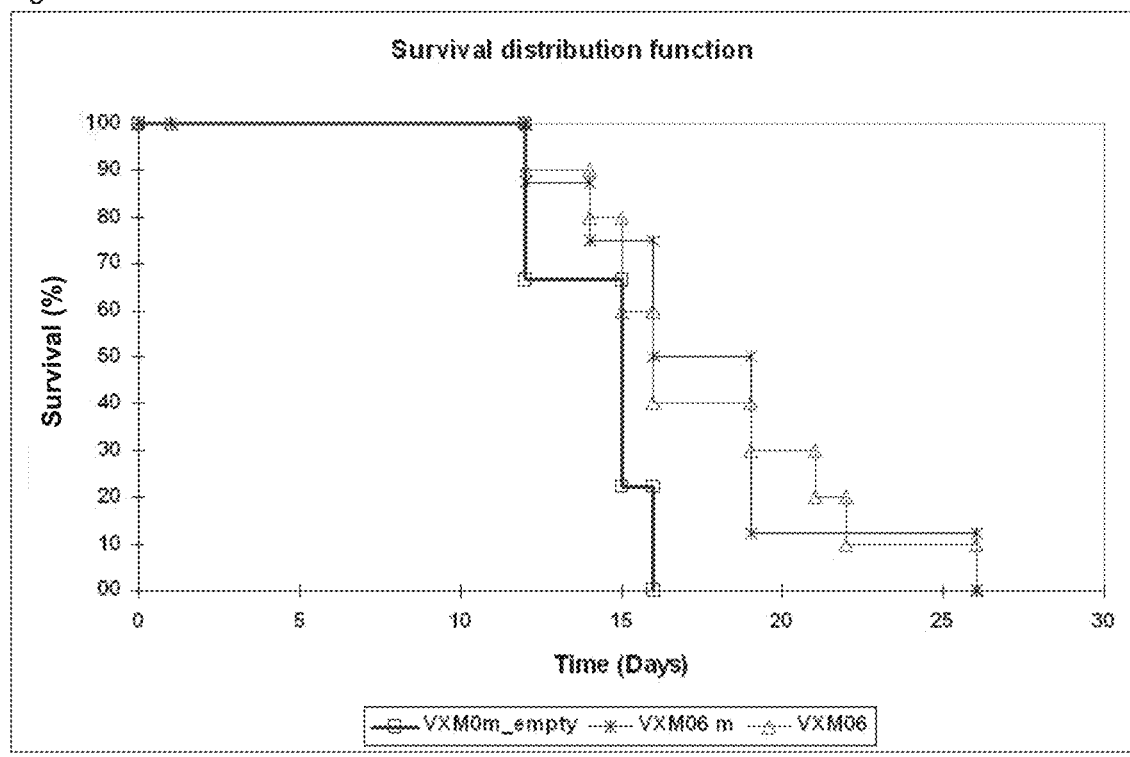

FIG. 4: Kaplan-Meier survival curves of mice bearing FBL-3 leukemia treated with VXM0m_empty, VXM06m and VXM06

Figure 5:
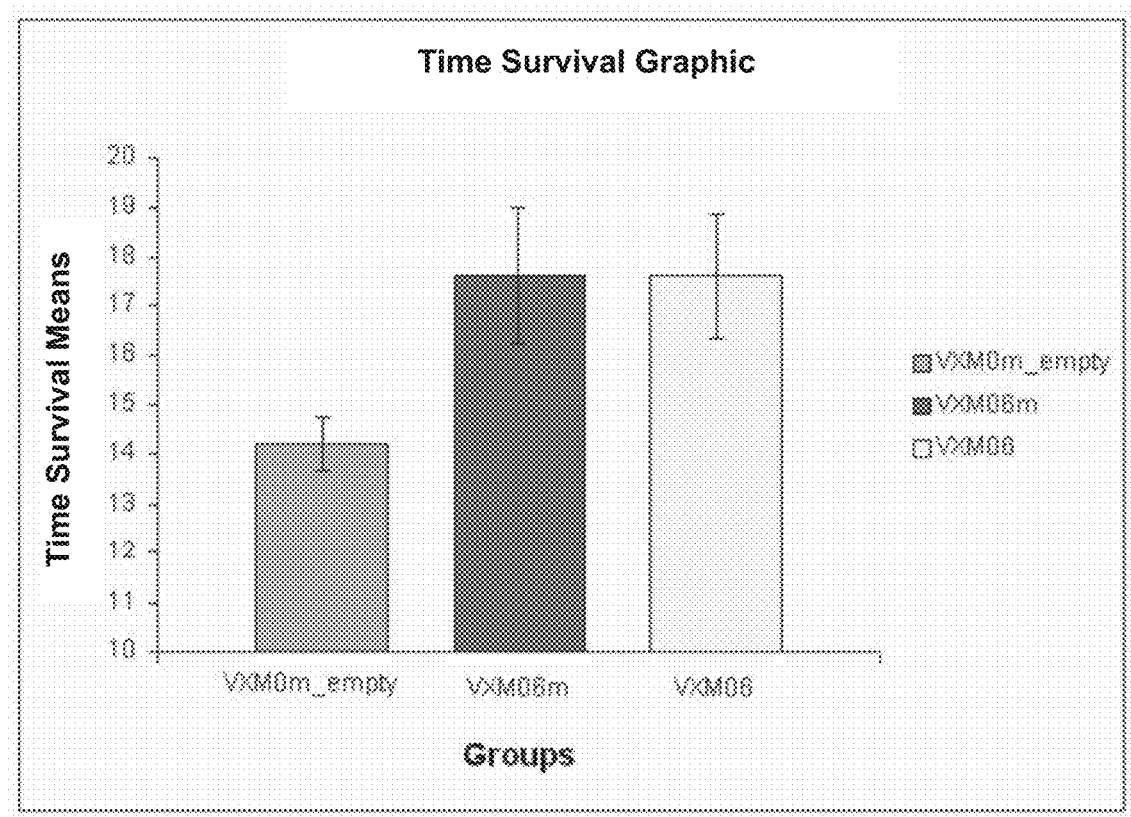

FIG. 5: Mean survival of mice bearing FBL-3 leukemia treated with VXM0m_empty, VXM06m and VXM06

Table 1: In vitro gene synthesis: phosphorylation reaction setup

Table 2: In vitro gene synthesis: amplification of ligation product—PCR profile

Table 3: Vaccine compositions

Table 4: Assessment of antitumor activity—experimental design

Table 5: Survival of mice bearing FBL-3 leukemia treated with VXM0m_empty, VXM06m and VXM06

Table 6: Number of dead animals after tumor challenge over time

Table 7: Mean and median survival of mice bearing FBL-3 leukemia treated with VXM0m_empty, VXM06m and VXM06

EXAMPLES

Example 1: Preparation of Recombinant Plasmids pVAX10.mWT1 and pVAX10.hWT1

Human truncated WT1 (1116 bp, WT1 sequence according to UniProt reference sequence P19544-7, truncated by the zinc finger domain) and murine truncated WT1 (1101 bp, WT1 sequence according to UniProt reference sequence P22561-5, truncated by the zinc finger domain) were cloned into the pVAX10 backbone derived of pVAX10.VR2-1.

WT1 DNA fragments were generated by double-strand gene synthesis, where oligonucleotides were linked together using a thermostable ligase.

Oligo Design and Synthesis:

In a first step, the gene sequence of truncated human and truncated murine WT1 (truncated by the zinc finger domain) were subdivided into individual oligonucleotides of 40 to 50 bases using the software "SeqEditor" (Entelechon). The defined oligonucleotides overlapped and corresponded to both DNA strands. After synthesis of the oligonucleotides of both DNA strands, the oligonucleotides were diluted with 10 mM Tris (pH 8.5) to a final concentration of 50 pmol/µl.

Kinase Reaction:

The in vitro synthesized oligonucleotides were then phosphorylated by incubation with T4 polynucleotide kinase in order to allow for subsequent ligation of the oligonucleotides. Forward and reverse oligonucleotides were phosphorylated.

The reaction setup is summarized in the following Table 1:

| Volume | Ingredient |
| --- | --- |
| 10 µl | Primer mix |
| 10 µl | 10x T4 Polynucleotide kinase (PNK) buffer |
| 10 µl | ATP (25 mM) |
| 68 µl | Sterile water |
| 2 µl | T4 PNK (10 U/µl) |

The reaction mixture was incubated for 1 hour at 37° C. in a water bath. Then the T4 polynucleotide kinase was inactivated by a five-minute heat step at 95° C. and afterwards immediately cooled on ice until further treatment.

12.5 µL of the kinase mixture was used directly for ligation (20 U Taq DNA ligase, 35 µl reaction volume (New England Biolabs, M0208S).

The denaturation step at 95° C. was followed by progressive cooling (1° C./min). During this process, the complementary oligonucleotides assemble to a double strand DNA. The process was performed in a thermocycler (Personal Cycler, Biometra). By addition of the thermostable Taq DNA ligase, the 5'-PO$_4$-end of the oligonucleotides were linked with the free 3'-OH-end of the following oligonucleotide. By repeated denaturation and renaturation steps, mismatched oligonucleotides were released. At the end of the program, the mixture was cooled at 4° C.

Amplification of the Ligation Products by PCR:

5 µl of the obtained ligation products (about 1.1 kb) were amplified by PCR in a 50 µl volume with flanking primers as depicted in the following Table 2:

| no | step | temperature | time | No of cycles |
| --- | --- | --- | --- | --- |
| 1 | denaturation | 95° C. | 5 min | 1 |
| 2 | denaturation | 95° C. | 30 sec | |
| 3 | annealing | 57° C. | 30 sec | 30x |
| 4 | elongation | 72° C. | 90 sec | |
| 5 | extra-elongation | 72° C. | 5 min | 1 |
| 6 | cooling | 4° C. | ∞ | 1 |

The PCR mixture contained the following components: 0.2-0.5 µM of each primer, 20 mM Tris-Cl, pH 8.8, 10 mM KCl, 10 mM (NH$_4$)$_2$SO$_4$, 2 mM MgSO$_4$, 0.1% Triton X-100, 25 mM dNTP (each), 2 U Vent$_R$ polymerase.

The in vitro synthesized DNA fragments (human and murine truncated WT1; about 1.1 kb each) were cloned into the pVAX10 backbone via NheI/XhoI (the VEGFR-2 coding region of recombinant plasmid pVAX10.VR2-1 was replaced by truncated human or murine WT1). For quality control, the entire plasmids were sequenced and aligned to the respective reference sequence after transformation into E. coli. Both sequences proved to be free of errors. The resulting plasmids were designated pVAX10.mWT1 and pVAX10.hWT1.

Example 2: Transformation of Attenuated Salmonella Strains with the Recombinant Plasmids S. typhi Ty 21a was transformed with plasmid pVAX10.hWT1. S. typhimurium SL7207 (aroA$^-$) was transformed with plasmid pVAX10.mWT1. The transformation was performed by electroporation.

Preparation of Competent Salmonella Cells:

Glycerol cultures of S. typhi Ty21a and S. typhimurium SL7207 were inoculated on LB plates (animal component free [ACF] soy peptone). The plates were incubated at 37° C. overnight. One colony each was used for overnight-liquid-preculture. 3 ml LB medium (ACF soy peptone) inoculated with one colony each was incubated at 37° C. and 180 rpm overnight. To prepare competent cells, 2×300 ml of LB medium (ACF soy peptone) were inoculated with 3 ml of the overnight culture and incubated at 37° C. and 180 rpm up to an OD$_{600}$ of about 0.5. The cultures were then put on ice for 10 minutes. Subsequently, the bacteria were centrifuged for 10 minutes at 3000×g at 4° C. and each pellet was resuspended in 500 mL of ice cold H$_2$O$_{dest}$. After a new centrifugation step, the bacterial pellets were washed twice in 10% ice cold glycerol. Both pallets were put together in 2 ml of 10% glycerol and finally frozen in aliquots of 50 µL on dry ice. The used glycerol did not contain any animal ingredients (Sigma Aldrich, G5150).

Transformation of Competent Salmonella Cells:

For each transformation reaction, a 50 µl aliquot of competent cells was thawed on ice for 10 minutes. After adding 3-5 µL of plasmid DNA (pVAX10.hWT1 for competent S. typhi Ty21a cells and pVAX10.mWT1 for competent S. typhimurium SL7207 cells) the mixtures were incubated on ice for five minutes. Subsequently, the mixtures were transferred to pre-cooled cuvettes (1 mm thickness). The electric pulse was carried out at 12.5 kV/cm. Immediately afterwards, 1 ml of LB medium (ACF soy peptone) was added to the cells, the cells were transferred into a 2 ml Eppendorf tube and shaken for 1 hour at 37° C. After a short centrifugation step on a bench centrifuge (16600 rcf, 20s), the bacterial pellet was resuspended in 200 µl of LB (ACF soy peptone) antibiotic-free medium. The mixtures were applied with a Drigalski spatula on LB plates (ACF soy peptone) containing kanamycin (concentration=25 µg/ml or 50 µg/ml). The plates were incubated at 37° C. overnight.

Plasmid Preparation of Recombinant Salmonella Clones:

Three clones of each recombinant Salmonella strain were incubated overnight in 3 ml of LB medium (ACF soy peptone) containing kanamycin (50 µg/ml) at 37° C. The bacterial culture was then pelleted by centrifugation (16600 rcf, 30 s). Plasmid isolation was performed using the NucleoSpin Plasmid Kit from Macherey-Nagel. The plasmid DNA was eluted from the silica gel columns with 50 µl water. 5 µl of the eluate was used in agarose gel electrophoresis for control.

For long-term storage, 1 ml glycerol cultures of the positive clones were produced. For this purpose, 172 µl glycerol (no animal ingredients) was added to 828 µl medium of a logarithmically growing 3 ml culture in a 1 low ml screw microtube. The samples were stored at −70° C. until further use.

Complete Sequencing of Recombinant Plasmid DNA Isolated from *Salmonella*:

3 ml of liquid LB-Kan medium (ACF soy peptone) were inoculated with one colony of recombinant *Salmonella* (*S. typhi* Ty21a harboring pVAX10.hWT1 and *S. typhimurium* SL7207 harboring pVAX10.mWT1) and incubated overnight at 37° C. and 180 rpm. The overnight culture was pelleted by centrifugation at 1300 rpm for 30 s on a bench centrifuge (Biofuge pico, Heraeus). The plasmid isolation was performed with the NucleoSpin Plasmid Kit from Macherey-Nagel. After alkaline lysis and precipitation of high molecular weight genomic DNA and cellular components, the plasmid DNA was loaded onto columns with a silica membrane. After a washing step, the plasmids were eluted from the column with 50 µl of sterile water and sequenced. The sequences were then compared with the respective reference sequence by clone specific alignments, i.e. the plasmid sequences of each *Salmonella* clone was one by one aligned with the reference sequence. All sequences were in line with the respective reference sequences. The recombinant *Salmonella* strains were designated VXM06 (*S. typhi* Ty21a harboring plasmid pVAX10.hWT1) and VXM06m (*S. typhimurium* SL7207 harboring plasmid pVAX10.mWT1).

Example 3: Assessing Antitumor Activity of VXM06 and VXM06m in Syngeneic Leukemia Mouse Model The efficacy of VXM06 and VXM06m was assessed in a syngeneic leukemia C57/BL6J mouse model over a period of 43 days (with dose administration on alternate days for 4 occasions followed by leukemia cell inoculation at day 17). Two groups, each comprising 10 male mice (n=10) either received VXM06 (*S. typhi* Ty21a containing pVAX10.hWT1 coding for truncated human WT1) or VXM06m (*S. typhimurium* containing pVAX10.mWT1 coding for truncated murine WT1) at doses of $10^{10}$ CFU/occasion. One similarly constituted control group received VXM0m_empty (*S. typhimurium* vector control with no expression plasmid) at the same dose as the treated groups. During the study, body weight, mortality, and survival investigations were undertaken. Prior to this main study, a pilot study over 14 days in male C57616 mice (n=5 per group) without vaccination was performed using $5.0 \times 10^6$ and $3.0 \times 10^7$ FBL-3 cells, after which the first cell concentration was judged as optimal for the main vaccination study.

DNA Vaccines:

VXM06, VXM06m, and the *S. typhimurium* empty vector (VXM0m_empty) without expression plasmid were stored at ≤−80° C. until use. Vials being used during vaccination were not frozen again but discarded afterwards. The DNA vaccines under investigation are characterized in the following Table 3:

| Test item | Batch | Concentration | Quantity |
|---|---|---|---|
| VXM0m_empty | VXM01m-e.1-01/2010 | $10^{11}$ CFU/ml | 0.7 ml/vial (10 vials) |
| VXM06m | VXM06m-031.1-01/2012 | $10^{11}$ CFU/ml | 0.7 ml/vial (10 vials) |
| VXM06 | VXM06-031.1-01/2012 | $10^{11}$ CFU/ml | 0.7 ml/vial (10 vials) |

Route of Drug Administration:

100 µl of VXM0m_empty, VXM06m and VXM06 were applied per animal and application. After thawing of test items, application took place within 30 min. All test substances were administered by oral gavage (per os, P.O) via cannula with an injection volume of 100 µl/mouse.

Regardless of animal groups, each animal received pre-dose application buffer to neutralize acid medium in the stomach prior to dosing (100 µl/animal/application for all dose groups). This buffer contained 2.6 g sodium hydrogen carbonate, 1.7 g L-ascorbic acid, 0.2 g lactose monohydrate and 100 ml of drinking water. Pre-dose applications were performed up to 30 minutes prior to application of the test items.

Cell Culture:

The WT1 overexpressing mouse leukemia cells FBL-3 required passaging to ensure viability and to attain the required amount of cells.

The exponentially growing tumor cells were collected, mixed with trypan blue (at the recommended dilution 1:1) for viability determination, and manually counted using a counting chamber under optical microscope. FBL-3 cells were washed and resuspended in serum-free RPMI medium for injections into C57BL/6 mice.

Vaccination and Tumor Cell Inoculation:

Cell injection conditions for intraperitoneal (I.P.) injection: cell viability ≥97%; $5.0 \times 10^6$ cells/500 µl/mouse.

Animals (30 C57BL/6 mice, 4-6 weeks, male, ≈20 g each, Charles River, France) were numbered, given a unique animal identification ear notch mark; the body weight was measured twice a week.

Ten mice each (n=10 male) were vaccinated with VXM0m_empty, VXM06m, and VMX06. Vaccination was carried out by oral gavage of $10^{10}$ CFU/application at days 1, 3, 5, and 7. At day 17, FBL-3 tumor cells were inoculated in mice by I.P. route. The experimental design is summarized in the following Table 4:

| Group | Animals | Tumor cells | Treatment | Dose (CFU/adm) | Admin. route | Treatment schedule |
|---|---|---|---|---|---|---|
| 1 | 10 | $5 \times 10^6$ | VXM0m_empty | $10^{10}$ (in 100 µl) | PO | Q2D × 4 (D1, D3, D5, D7) |
| 2 | 10 | $5 \times 10^6$ | VXM06m | $10^{10}$ (in 100 µl) | PO | Q2D × 4 (D1, D3, D5, D7) |
| 3 | 10 | $5 \times 10^6$ | VXM96 | $10^{10}$ (in 100 µl) | PO | Q2D × 4 (D1, D3, D5, D7) |

Results:

Survival data for the three treatment groups are listed in the following Table 5:

| Day | Group 1;<br>VXM0m_empty<br>Survival | Group 2;<br>VXM06m<br>Survival | Group 3;<br>VXM06<br>Survival |
|---|---|---|---|
| −3 | 10 | 10 | 10 |
| 1 | 10 | 10 | 10 |
| 5 | 9 | 9 | 10 |
| 7 | 9 | 9 | 10 |
| 12 | 9 | 9 | 10 |
| 15 | 9 | 9 | 10 |
| 19 | 9 | 8 | 10 |
| 22 | 9 | 8 | 10 |
| 26 | 9 | 8 | 10 |
| 29 | 5 | 7 | 9 |
| 33 | 0 | 4 | 4 |
| 36 | 0 | 1 | 3 |
| 40 | 0 | 1 | 1 |
| 43 | 0 | 0 | 0 |

A daily clinical examination of all animals was performed: behavior, signs of suffering (cachexia, becoming, and difficulties moving or feeding).

The number of dead animals after tumor challenge are listed in the following Table 6:

| Time | Survival | Dead | treatment |
|---|---|---|---|
| 1 | 9 | 0 | VXM0m_empty |
| 12 | 6 | 3 | VXM0m_empty |
| 15 | 2 | 4 | VXM0m_empty |
| 16 | 0 | 2 | VXM0m_empty |
| 1 | 8 | 0 | VXM06m |
| 12 | 7 | 1 | VXM06m |
| 14 | 6 | 1 | VXM06m |
| 16 | 4 | 2 | VXM06m |
| 19 | 1 | 3 | VXM06m |
| 26 | 0 | 1 | VXM06m |
| 1 | 10 | 0 | VXM06 |
| 12 | 9 | 1 | VXM06 |
| 14 | 8 | 1 | VXM06 |
| 15 | 6 | 2 | VXM06 |
| 16 | 4 | 2 | VXM06 |
| 19 | 3 | 1 | VXM06 |
| v21 | 2 | 1 | VXM06 |
| 22 | 1 | 1 | VXM06 |
| 26 | 0 | 1 | VXM06 |

FIG. 4 depicts Kaplan-Meier survival curves of mice bearing FBL-3 leukemia treated with VXM0m_empty, VXM06m and VXM06. Mice treated with VXM06m and VXM06 survived longer compared to the control mice (up to 26 days). About 40% the mice that received VXM06m and VXM06 survived longer than those treated with VXM0m_empty. Mean and median survival of the three test groups are depicted in the following Table 7:

| Mice | VXM0m_empty<br>9 | VMX06m<br>8 | VXM06<br>10 |
|---|---|---|---|
|  |  | Survival time |  |
| 1 | 12 | 12 | 12 |
| 2 | 12 | 14 | 14 |
| 3 | 12 | 16 | 15 |
| 4 | 15 | 16 | 15 |
| 5 | 15 | 19 | 16 |
| 6 | 15 | 19 | 16 |
| 7 | 15 | 19 | 19 |
| 8 | 16 | 26 | 21 |
| 9 | 16 |  | 22 |
| 10 |  |  | 26 |
| Median | 15 | 17.5 | 16 |
| Mean | 14.2 | 17.6 | 17.6 |
| SD | 1.6 | 4.0 | 4.1 |
| SEM | 0.5 | 1.4 | 1.3 |
| Var. | 2.6 | 15.7 | 16.6 |

FIG. 5 depicts the mean survival of mice bearing FBL-3 leukemia treated with VXM0m_empty, VXM06m and VXM06. Mice treated with VXM06m and VXM06 survived longer compared to the control mice.

This study demonstrated the effectiveness of the constructs VXM06 and VXM06m in targeting WT1 overexpressing leukemia cells in a mouse model. The control mice treated with empty vector survived for up to 16 days after tumor cell challenge (see FIG. 4). In contrast, the mice treated with VXM06m or with VXM06 showed prolonged survival compared to the mice vaccinated with the control vector VXM0m_empty (up to 26 days for both test items). About 40% of the mice that received VXM06m or VXM06 survived longer than those in the control group treated with VXM0m_empty.

In summary, VXM06m and VXM06 showed a pharmacodynamic effect on the survival of test animals in this syngeneic C57616 leukemia mouse model. A similar pharmacodynamic effect of the two compounds VXM06m and VXM06 compared to empty vector was observed. These results show that these vaccines were able to trigger a response against WT1 in an immune-competent mouse leukemia model resulting in longer survival of animals compared to animals treated with empty vector.

The invention claimed is:

1. A method of treating a Wilms' Tumor Protein (WT1) expressing cancer, comprising administering orally to a subject a DNA vaccine comprising an attenuated mutant strain of *Salmonella enterica typhi* Ty21a comprising at least one copy of a recombinant DNA molecule comprising a eukaryotic expression cassette encoding WT1 in cancer immunotherapy, wherein the vaccine is not HLA-restricted.

2. The method of claim 1, wherein WT1 is human WT1.

3. The method of claim 1, wherein the recombinant DNA molecule comprises a kanamycin antibiotic resistance gene, a pMB1 ori, and a eukaryotic expression cassette encoding human WT1 under the control of a CMV promoter.

4. The method of claim 1, wherein the cancer immunotherapy further comprises administration of one or more further attenuated mutant strain(s) of *Salmonella* comprising at least one copy of a recombinant DNA molecule comprising an expression cassette encoding a tumor antigen and/or a tumor stroma antigen.

5. The method of claim 4, wherein the attenuated mutant strain of *Salmonella* is co-administered with said one or more further attenuated mutant strain(s) of *Salmonella*.

6. The method of claim 1, wherein cancer immunotherapy is accompanied by chemotherapy, radiotherapy or biological cancer therapy.

7. The method of claim 1, wherein the cancer is selected from leukemia and solid tumors.

8. The method of claim 1, wherein the attenuated mutant strain of *Salmonella* is administered as the single dose comprising from about $10^5$ to about $10^{11}$ colony forming units (CFU).

9. The method of claim 1, for individualized cancer immunotherapy comprising a step of assessing a tumor antigen expression pattern and/or stroma antigen expression pattern of the subject.

10. The method of claim 1, wherein WT1 is truncated and the truncated WT1 has the amino acid sequence as found in SEQ ID NO 1.

11. The method of claim 4, wherein said one or more further attenuated mutant strain(s) of *Salmonella* is/are *Salmonella typhi* Ty21a comprising a eukaryotic expression cassette.

12. The method of claim 11, wherein said one or more further attenuated mutant strain(s) of *Salmonella* comprise(s) an attenuated mutant strain of *Salmonella* encoding human VEGFR-2.

13. The method of claim 7, wherein the leukemia is selected from acute myeloid leukemia (AML) and acute lymphoid leukemia (ALL).

14. The method of claim 7, wherein the solid tumor is selected from lung cancer, breast cancer, esophageal, colon, colorectal, gastric, cholangioductal, pancreatic cancer, glioblastoma, head and neck cancer, synovial sarcoma, angiosarcoma, osteosarcoma, thyroid cancer, cervical, endometrial, ovarian cancer, neuroblastoma, rhabdomyosarcoma and prostate cancer.

* * * * *

SEQUENCE LISTING

<160> NUMBER OF SEQ ID NOS: 2

<210> SEQ ID NO 1
<211> LENGTH: 371
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

```
Gln Trp Ala Pro Val Leu Asp Phe Ala Pro Pro Gly Ser Ala Tyr
         35                  40                  45

Gly Ser Leu Gly Gly Pro Ala Pro Pro Ala Pro Pro Pro Pro Pro
 50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
                100                 105                 110

Gly Pro Pro Pro Ser Gln Ala Ser Ser Gly Gln Ala Arg Met Phe
                115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Pro Val Tyr Gly Cys His Thr Pro Thr Asp Ser
                195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
                275                 280                 285

His Thr His Gly Val Phe Arg Gly Ile Gln Asp Val Arg Arg Val Pro
                290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
                355                 360                 365

Gln Leu Lys
 370

<210> SEQ ID NO 2
<211> LENGTH: 4616
<212> TYPE: DNA
<213> ORGANISM: artificial sequence
<220> FEATURE:
<223> OTHER INFORMATION: nucleic acid sequence of plasmid pVAX10.hWT1

<400> SEQUENCE: 2
tgggcttttg ctggcctttt gctcacatgt tcttgactct tcgcgatgta cgggccagat      60
atacgcgttg acattgatta ttgactagtt attaatagta atcaattacg gggtcattag     120
```

```
ttcatagccc atatatggag ttccgcgtta cataacttac ggtaaatggc ccgcctggct    180
gaccgcccaa cgaccccgc ccattgacgt caataatgac gtatgttccc atagtaacgc    240
caatagggac tttccattga cgtcaatggg tggactattt acggtaaact gcccacttgg    300
cagtacatca agtgtatcat atgccaagta cgccccctat tgacgtcaat gacggtaaat    360
ggcccgcctg gcattatgcc cagtacatga ccttatggga ctttcctact ggcagtaca    420 tctacgtatt agtcatcgct attaccatgg tgatgcggtt ttggcagtac atcaatgggc    480
gtggatagcg gtttgactca cggggatttc caagtctcca ccccattgac gtcaatggga    540
gtttgttttg gcaccaaaat caacgggact ttccaaaatg tcgtaacaac tccgccccat    600
tgacgcaaat gggcggtagg cgtgtacggt gggaggtcta tataagcaga gctctctggc    660
taactagaga acccactgct tactggctta tcgaaattaa tacgactcac tatagggaga    720
cccaagctgg ctagcatgga cttcctcttg ctgcaggacc cggcttccac gtgtgtcccg    780
gagccggcgt ctcagcacac gctccgctcc gggcctgggt gcctacagca gccagagcag    840
cagggagtcc gggacccggg cggcatctgg gccaagttag gcgccgccga ggccagcgct    900
gaacgtctcc agggccggag gagccgcggg gcgtccgggt ctgagccgca gcaaatgggc    960
tccgacgtgc gggacctgaa cgcgctgctg cccgccgtcc cctccctggg tggcggcggc   1020
ggctgtgccc tgcctgtgag cggcgcggcg cagtgggcgc cggtgctgga ctttgcgccc   1080
ccgggcgctt cggcttacgg gtcgttgggc ggccccgcgc cgccaccggc tccgccgcca   1140
cccccgccgc cgccgcctca ctccttcatc aaacaggagc cgagctgggg cggcgcggag   1200
ccgcacgagg agcagtgcct gagcgccttc actgtccact tttccggcca gttcactggc   1260
acagccggag cctgtcgcta cgggccttc ggtcctcctc cgcccagcca ggcgtcatcc   1320
ggccaggcca ggatgtttcc taacgcgccc tacctgccca gctgcctgga gagccagccc   1380
gctattcgca atcagggtta cagcacggtc accttcgacg gacgcccag ctacggtcac   1440 acgccctcgc accatgcggc gcagttcccc aaccactcat tcaagcatga ggatcccatg   1500
ggccagcagg gctcgctggg tgagcagcag tactcggtgc cgccccggt ctatggctgc   1560 cacacccca ccgacagctg caccggcagc caggctttgc tgctgaggac gccctacagc   1620
agtgacaatt tataccaaat gacatcccag cttgaatgca tgacctggaa tcagatgaac   1680
ttaggagcca ccctaaaggg agttgctgct gggagctcca gctcagtgaa atggacagaa   1740
gggcagagca accacagcac agggtacgag agcgataacc acacaacgcc catcctctgc   1800
ggagcccaat acagaataca cacgcacggt gtcttcagag gcattcagtg actcgagtct   1860
agagggcccg tttaaacccg ctgatcagcc tcgactgtgc cttctagttg ccagccatct   1920
gttgtttgcc cctcccccgt gccttccttg accctggaag gtgccactcc cactgtcctt   1980
tcctaataaa atgaggaaat tgcatcgcat tgtctgagta ggtgtcattc tattctgggg   2040
ggtggggtgg ggcaggacag caagggggag gattgggaag acaatagcag gcatgctggg   2100
gatgcggtgg gctctatggc ttctactggg cggttttatg acagcaagc gaaccggaat   2160 tgccagctgg ggcgccctct ggtaaggttg ggaagccctg caaagtaaac tggatggctt   2220
tctcgccgcc aaggatctga tggcgcaggg atcaagctc tgatcaagag acaggatgag   2280
gatcgtttcg catgattgaa caagatggat tgcacgcagg ttctccggcc gcttgggtgg   2340
agaggctatt cggctatgac tgggcacaac agacaatcgg ctgctctgat gccgccgtgt   2400
tccggctgtc agcgcagggg cgcccggttc tttttgtcaa gaccgacctg tccggtgccc   2460
tgaatgaact gcaagacgag gcagcgcggc tatcgtggct ggccacgacg ggcgttcctt   2520
```

```
gcgcagctgt gctcgacgtt gtcactgaag cgggaaggga ctggctgcta ttgggcgaag      2580
tgccggggca ggatctcctg tcatctcacc ttgctcctgc cgagaaagta tccatcatgg      2640
ctgatgcaat gcggcggctg catacgcttg atccggctac ctgcccattc gaccaccaag      2700
cgaaacatcg catcgagcga gcacgtactc ggatggaagc cggtcttgtc gatcaggatg      2760
atctggacga agagcatcag gggctcgcgc cagccgaact gttcgccagg ctcaaggcga      2820
gcatgcccga cggcgaggat ctcgtcgtga cccatggcga tgcctgcttg ccgaatatca      2880
tggtggaaaa tggccgcttt tctggattca tcgactgtgg ccggctgggt gtggcggacc      2940
gctatcagga catagcgttg gctacccgtg atattgctga agagcttggc ggcgaatggg      3000
ctgaccgctt cctcgtgctt tacggtatcg ccgctcccga ttcgcagcgc atcgccttct      3060
atcgccttct tgacgagttc ttctgaatta ttaacgctta caatttcctg atgcggtatt      3120
ttctccttac gcatctgtgc ggtatttcac accgcataca ggtggcactt tcggggaaa       3180 tgtgcgcgga acccctattt gtttattttt ctaaatacat tcaaatatgt atccgctcat      3240
gagacaataa ccctgataaa tgcttcaata atagcacgtg ctaaacttc atttttaatt      3300 taaaaggatc taggtgaaga tcctttttga taatctcatg accaaaatcc cttaacgtga      3360
gttttcgttc cactgagcgt cagaccccca tcagtgacca aacaggaaaa aaccgccctt      3420
aacatggccc gctttatcag aagccagaca ttaacgcttc tggagaaact caacgagctg      3480
gacgcggatg aacaggcaga catctgtgaa tcgcttcacg accacgctga tgagctttac      3540
cgcagctgcc tcgcgcgttt cggtgatgac ggtgaaaacc tctgacacat gcagctcccg      3600
gagacggtca cagcttgtct gtaagcggat gccgggagca gacaagcccg tcagggcgcg      3660
tcagcgggtg ttggcgggtg tcggggcgca gccatgaccc agtcacgtag cgatagcgga      3720
gtgtatactg gcttaactat gcggcatcag agcagattgt actgagagtg caccatatgc      3780
ggtgtgaaat accgcacaga tgcgtaagga gaaaataccg catcaggcgc tcttccgctt      3840
cctcgctcac tgactcgctg cgctcggtcg ttcggctgcg gcgagcggta tcagctcact      3900
caaaggcggt aatacggtta tccacagaat caggggataa cgcaggaaag aacatgtgag      3960
caaaaggcca gcaaaaggcc aggaaccgta aaaaggccgc gttgctggcg ttttccata       4020 ggctccgccc ccctgacgag catcacaaaa atcgacgctc aagtcagagg tggcgaaacc      4080
cgacaggact ataaagatac caggcgtttc ccctggaag ctccctcgtg cgctctcctg       4140
ttccgaccct gccgcttacc ggatacctgt ccgcctttct cccttcggga agcgtggcgc      4200
tttctcatag ctcacgctgt aggtatctca gttcggtgta ggtcgttcgc tccaagctgg      4260
gctgtgtgca cgaaccccc gttcagcccg accgctgcgc cttatccggt aactatcgtc       4320
ttgagtccaa cccggtaaga cacgacttat cgccactggc agcagccact ggtaacagga      4380
ttagcagagc gaggtatgta ggcggtgcta cagagttctt gaagtggtgg cctaactacg      4440
gctacactag aaggacagta tttggtatct gcgctctgct gaagccagtt accttcggaa      4500
aaagagttgg tagctcttga tccggcaaac aaaccaccgc tggtagcggt ggtttttttg      4560
tttgcaagca gcagattacg cgcagaaaaa aaggatctca agaagatcct ttgatc         4616
```